(12) United States Patent
Cole

(10) Patent No.: US 8,569,655 B2
(45) Date of Patent: Oct. 29, 2013

(54) WELDING HELMET WITH INTEGRAL USER INTERFACE

(75) Inventor: Stephen R. Cole, University Heights, OH (US)

(73) Assignee: Lincoln Global, Inc., City of Industry, CA (US)

( * ) Notice: Subject to any disclaimer, the term of this patent is extended or adjusted under 35 U.S.C. 154(b) by 951 days.

(21) Appl. No.: 12/577,824

(22) Filed: Oct. 13, 2009

(65) Prior Publication Data

US 2011/0083241 A1    Apr. 14, 2011

(51) Int. Cl.
  *B23K 9/095*  (2006.01)
  *B23K 9/32*   (2006.01)
  *A61F 9/06*   (2006.01)

(52) U.S. Cl.
  USPC .................... 219/147; 2/8.2; 345/8

(58) Field of Classification Search
  USPC ......... 219/130.01, 147; 2/8.2, 8.7, 8.8; 345/8; 348/158, 159
  See application file for complete search history.

(56) References Cited

U.S. PATENT DOCUMENTS

| | | | | |
|---|---|---|---|---|
| 3,059,519 A | * | 10/1962 | Stanton | 359/482 |
| 4,375,026 A | * | 2/1983 | Kearney | 219/130.01 |
| 4,677,277 A | | 6/1987 | Cook et al. | |
| 5,089,914 A | * | 2/1992 | Prescott | 2/5 |
| 5,266,930 A | | 11/1993 | Ichikawa et al. | |
| 5,751,258 A | * | 5/1998 | Fergason et al. | 345/7 |
| 5,835,277 A | * | 11/1998 | Hegg | 359/630 |
| 6,242,711 B1 | * | 6/2001 | Cooper | 219/147 |
| 6,560,029 B1 | | 5/2003 | Dobbie et al. | |
| 6,583,386 B1 | | 6/2003 | Ivkovich | |
| 6,710,298 B2 | * | 3/2004 | Eriksson | 219/147 |
| 6,734,393 B1 | * | 5/2004 | Friedl et al. | 219/147 |
| 6,788,442 B1 | * | 9/2004 | Potin et al. | 345/8 |
| 2005/0007504 A1 | * | 1/2005 | Fergason | 2/8 |
| 2005/0017152 A1 | * | 1/2005 | Fergason | 250/205 |

FOREIGN PATENT DOCUMENTS

| | | | |
|---|---|---|---|
| DE | 4037879 A1 | | 6/1991 |
| DE | 19834205 A1 | * | 2/2000 |
| WO | 01/12376 A1 | | 2/2001 |
| WO | 01/58400 A1 | | 8/2001 |
| WO | WO-2005/102230 A1 | * | 11/2005 |

* cited by examiner

*Primary Examiner* — Geoffrey S Evans
(74) *Attorney, Agent, or Firm* — Hahn, Loeser & Parks, LLP

(57) ABSTRACT

A welding helmet is capable of providing an image representative of information from an associated welding operation where the image appears in the same focal range as the welding work area.

20 Claims, 6 Drawing Sheets

WELDING HELMET WITH INTEGRAL USER INTERFACE

TECHNICAL FIELD

This invention relates in general to equipment used in welding.

BACKGROUND

Welding is an important process in the manufacture and construction of various products and structures. Applications for welding are widespread and used throughout the world, for example, the construction and repair of ships, buildings, bridges, vehicles, and pipe lines, to name a few. Welding may performed in a variety of locations, such as in a factory with a fixed welding operation or on site with a portable welder.

In manual or semi-automated welding a user/operator (i.e. welder) directs welding equipment to make a weld. For example, in arc welding the welder may manually position a welding rod or welding wire and produce a heat generating arc at a weld location. In this type of welding the spacing of the electrode from the weld location is related to the arc produced and to the achievement of optimum melting/fusing of the base and welding rod or wire metals. The quality of such a weld is often directly dependent upon the skill of the welder.

Welders generally rely upon a variety of information when welding. This information includes, for example, current and voltage. Traditionally, welders would need to look at gauges on the control panel of the welding equipment to gain this information. This would require the welder to direct their field of vision away from the welding work area and as such was undesirable.

In the past, efforts have been made to provide welders with information during welding, such as in the method disclosed in U.S. Pat. No. 4,677,277, where current and voltage are monitored to produce an audio indication to the operator as to the condition of the arc in arc welding. However, monitors consisting only of audio arc parameter indicators are hard to hear and interpolate and are not capable of achieving the desired closeness of control and quality of weld often required.

More recently, as disclosed in U.S. Pat. No. 6,242,711, an apparatus for monitoring arc welding has been developed that provides a welder with real-time voltage and current conditions of the welding arc where information in the form of lights, illuminated bar graphs, light projections, illuminated see-through displays, or the like are placed within the visual range of the helmet wearing operator and located in proximity to the helmet viewing window in the helmet. However, in this apparatus a welder must still move their visual focus away from the welding work area in order to focus on the information located proximate to the welding window or the welder must accept the information peripherally while continuing to focus on the welding work area.

SUMMARY

This invention relates to a welding helmet that is capable of providing an image representative of information from an associated welding operation where the image appears in the same focal range as the welding work area.

Various aspects will become apparent to those skilled in the art from the following detailed description and the accompanying drawings.

DETAILED DESCRIPTION

Figure 1:
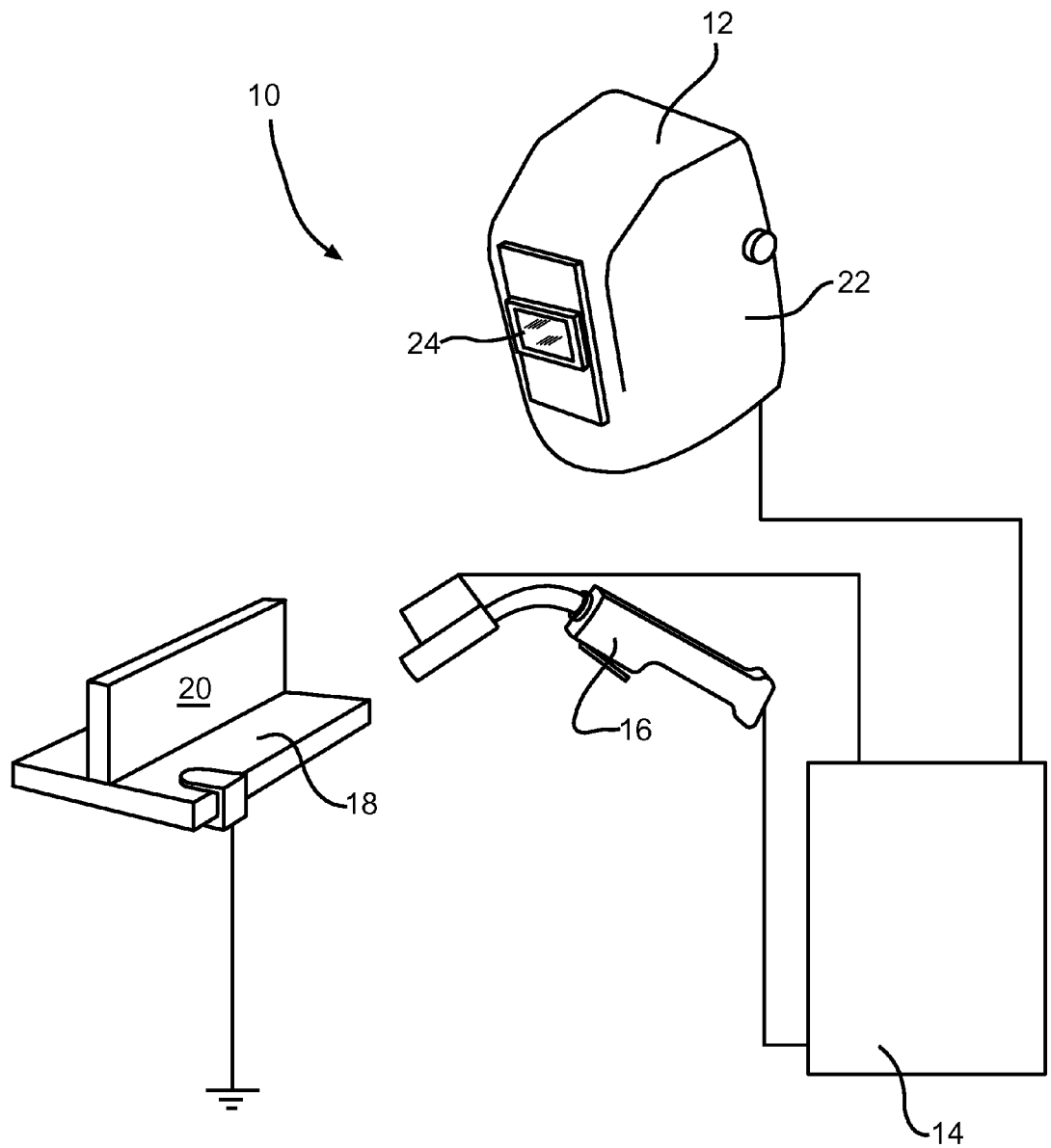
FIG. 1 is a schematic view of a welding system according to the present invention.

Referring now to the drawings, there is illustrated in FIG. 1 a welding system 10. The welding system 10 includes a welding helmet 12, a welding system 14, a welding gun 16 and a work piece 18. The work piece 18 generally defines a welding work are 20 where the welding gun 16 may be used to form a weld.

The welding system 14 includes welding equipment for generating a welding current and voltage, a welding control system for controlling the welding current and voltage, and a monitoring system for monitoring the welding current and voltage. The monitoring system may also monitor a variety of other operating parameter, such as but not limited to, wire feed speed, amount of wire used/amount of wire remaining, any type of welding feedback desired by the operator and any other desired operating parameter.

Figure 2:
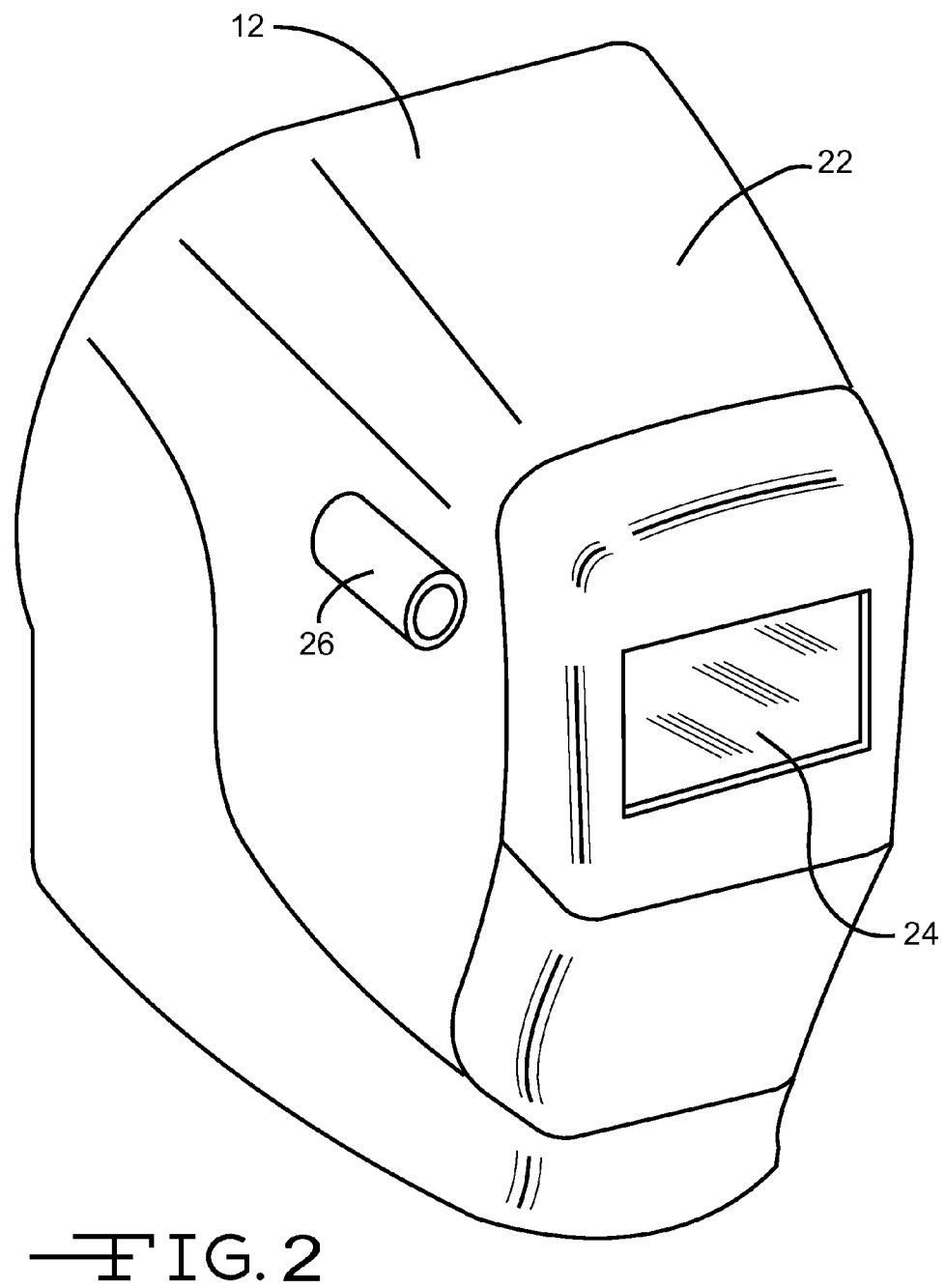
FIG. 2 is an enlarged view of a welding helmet similar to the helmet of FIG. 1 including a camera.

The welding helmet 12 includes a main body 22 with a visual display 24 connected to the main body 22. The display 24 may be a window including a welding lens, as shown in FIG. 1, a video monitor, as shown in FIG. 2, such as an LCD display or LED array, or any other device suitable to allow a welder to see the welding work area 20. It must be understood that in such an example where the display 24 is a video monitor video processing may be utilized to enhance the pictures of the welding operation. Further, recording devices may optionally be included to record and later playback welding operations for analysis and/or evaluation.

As best shown in FIG. 2, a welding helmet 12 may include a camera 26 mounted at or proximate to the point of view of the welder. In the example where the visual display 24 is a video monitor, the camera 26 may provide video pictures of the welding work area 20 to the display 24.

Figure 3:
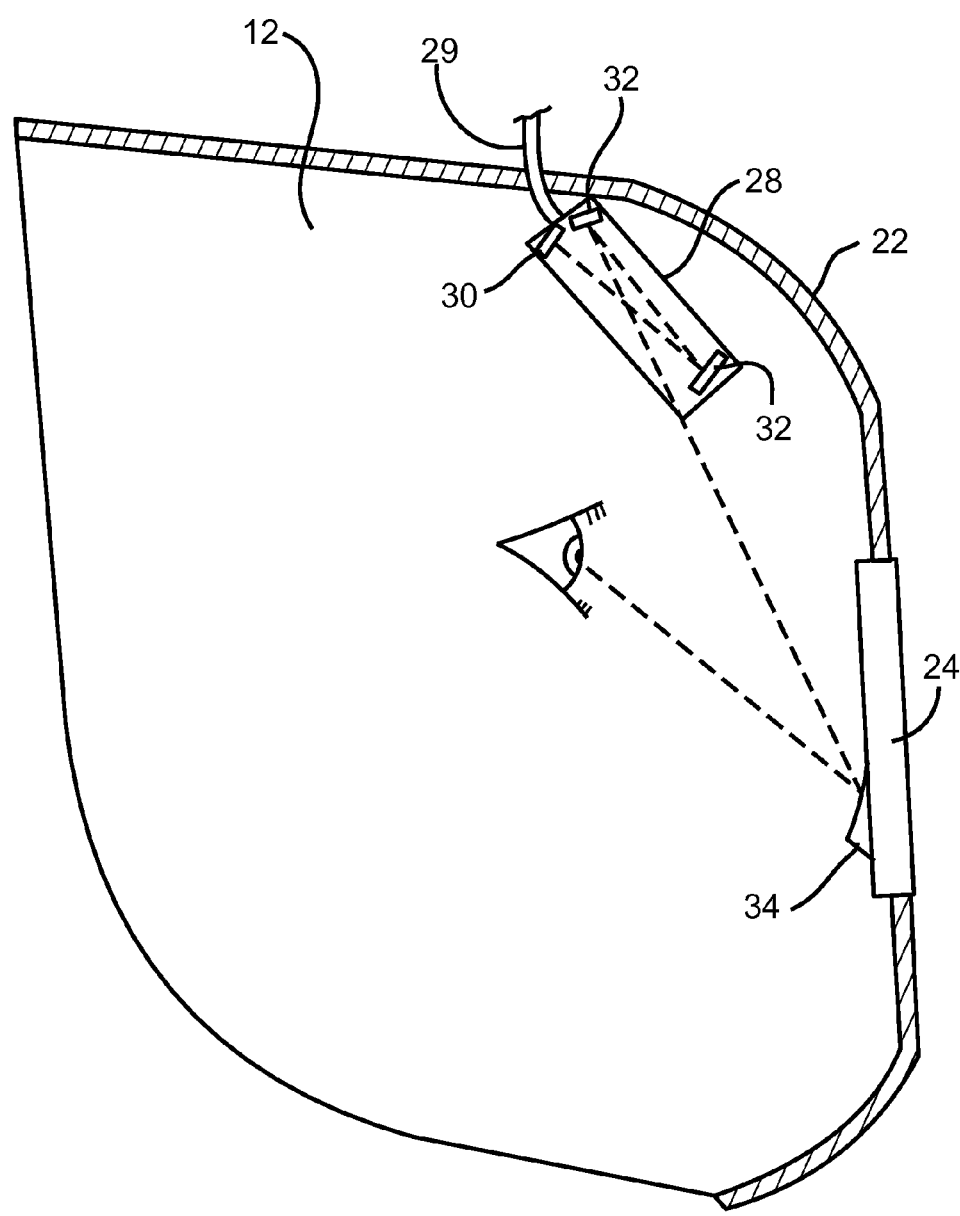
FIG. 3 is a cross-sectional diagram of a welding helmet similar to the helmet of FIG. 2 including a projector.
Figure 4:
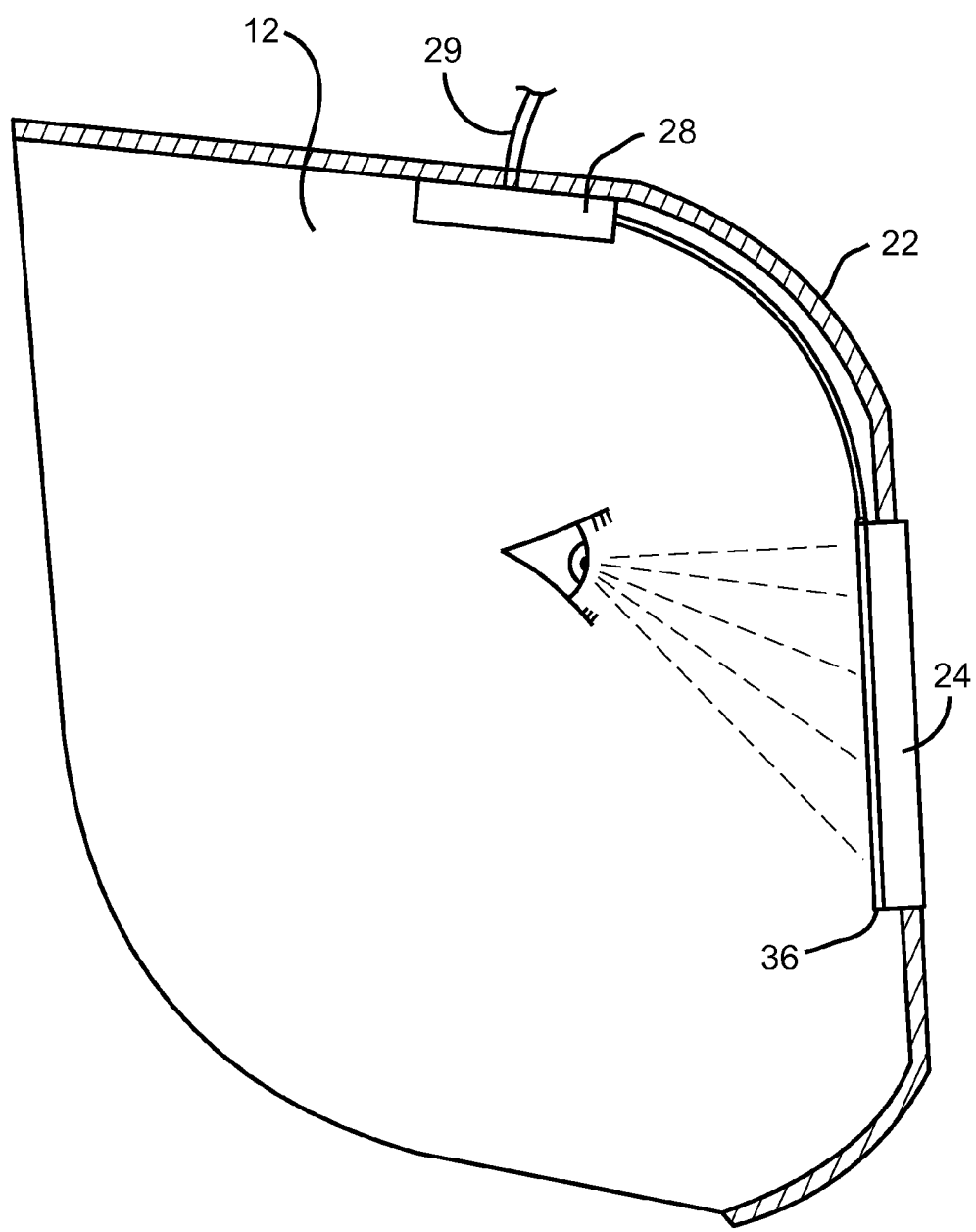
FIG. 4 is a cross-sectional diagram of a welding helmet similar to the helmet of FIG. 3 including an integrated video display.

As shown in FIGS. 3 and 4 an information generating mechanism 28 is in communication with the monitoring system of the welding system 14 and capable of generating an image representative of information from the monitoring system based upon the a monitored welding parameter, such as current and voltage upon the visual display 24 where the focus of the image is at a focus range with an associated welding work area, e.g. outside of the main body 22 of the welding helmet 12. For example, the image may be symbolic, alpha-numeric, or any other device suitable to indicate the information. Thus, a welder may view an image representative of information about a welding operation without removing focus from the work area. Thus, in at least one embodiment the welder may focus on the work area and the image of information at the same time.

It must be understood that among other types of information, along with a variety of other parameter, the information based upon welding current and voltage includes, but is not limited to, welding current feedback, welding voltage feedback, control settings of the welding equipment, statistical information of the welding process, benchmarks or limits including capacity representations, alerts including material shortage or low flow, a representation of an intended or desired weld, etc.

Further, in one embodiment, the camera 26 is used to calibrate the depth of the image relative to the welding work area 20. In another embodiment, positions sensors on the welding gun may be used to calibrate the depth of the image. In particular applications it is highly desirable to carefully align the image and the welding work are such that the information represented in the image is easy for the welder to access and such that the information in the image is readily accepted by the welder.

In the example where the visual display 24 is a video monitor, information generating mechanism 28 may include an image representative of information from the monitoring system based upon the monitored parameter, such as welding current and voltage, in video pictures of the welding work area 20 shown on the display 24.

As indicated at 29, the information generating mechanism 28 may be in wired or wireless communication with other devices as desired.

In FIG. 3, the information generating mechanism 28 is a projector 28. The projector may, for example, include an internal LCD display or LED array 30 along with a number of associated mirrors 32 to reflect the image generated to the visual display 24. The reflected image gives the image the appearance of depth relative to the visual display 24 and thus puts the image at a focus range with an associated welding work area and outside of the main body 22 of the welding helmet 12 and optionally at the same focal distance as the associated welding work area 20. Optionally, a reflective surface 34 may be placed upon a portion of the visual display 24 in order to achieve a desired amount of reflection or reflection angle. In one embodiment, teleprompter type technology may be utilized to place the image upon the display 24 or surface 34. Additionally, it must be understood that one embodiment includes the use of an LCD display or other similar display within the helmet to generate the image which is then sent along an optical path, such as by reflection or fiber optics or any other suitable device to place the image display 24 or surface 34.

In FIG. 4, the information generating mechanism 28 includes a screen, film, or sheet 36 integrated into the visual display 24. The sheet 36 may be a semi-transparent LCD film, electro-optic film, or any other suitable medium for the information generating mechanism 28 to produce an image generated in the visual display 24. In one application, the information generating mechanism 28 may projecting a stereogram on the welding lens such that a welder's eyes will separately view the images to create the perception of depth and thus focus the image at a focus range with the associated welding work area 20 and outside of the main body 22 of the welding helmet 12.

Figure 5:
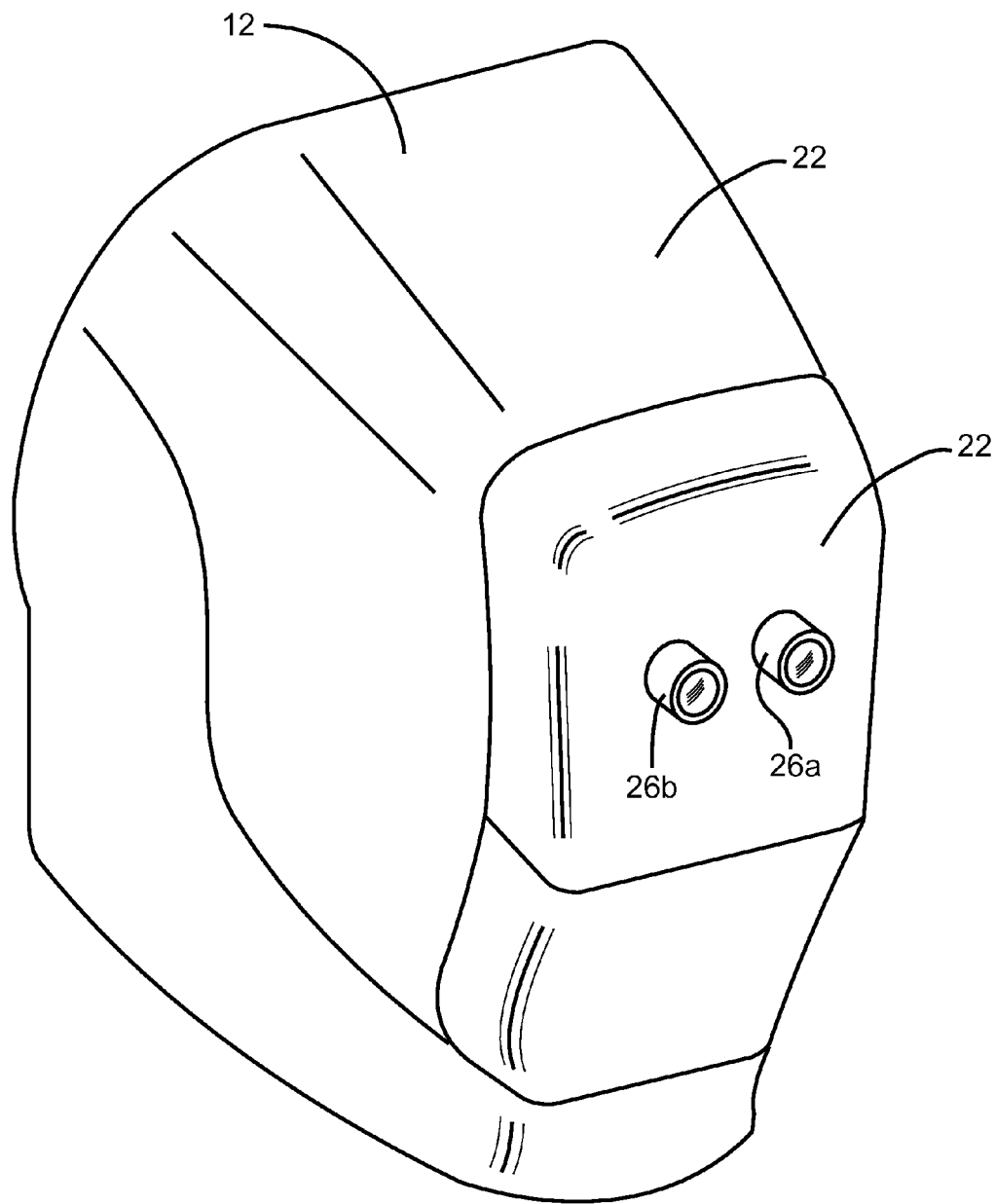
FIG. 5 is a perspective view of a welding helmet similar to the helmet of FIG. 2 including binocular cameras.
Figure 6:
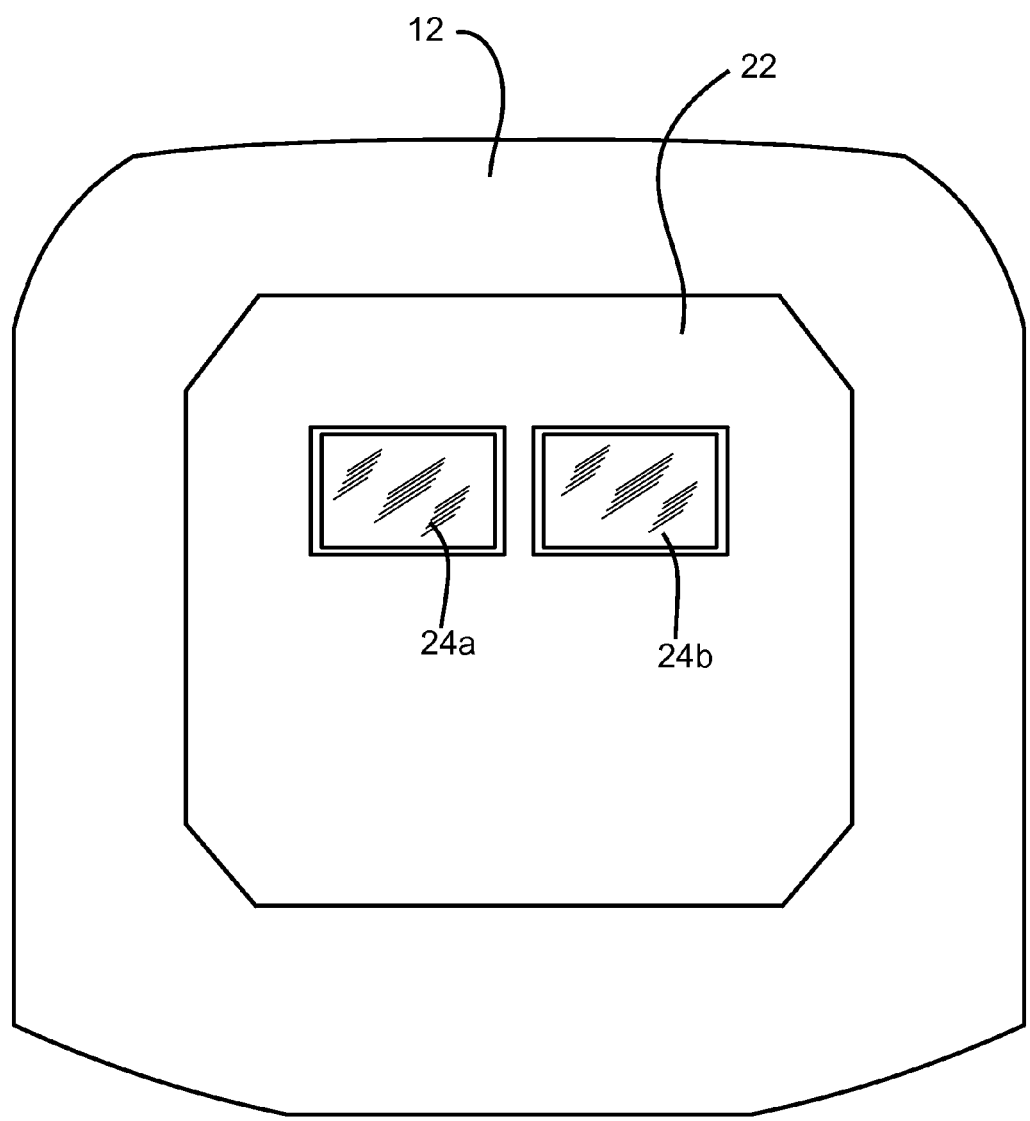
FIG. 6 is an interior view of a welding helmet similar to the helmet of FIG. 5 showing binocular viewing screens.

There is shown in FIG. 5 a welding helmet 12 including binocular cameras 26a and 26b. As shown in FIG. 6, these cameras 26a and 26b correspond to binocular viewing screens 24a and 24b. An information generating mechanism may produce an image to be generated in either of the viewing screens 24a or 24b or both. In one embodiment, the cameras 26a and 26b are placed in alignment with the screens 24a and 24b except on opposite sides of the main body 22, thus giving the welder the view directly in front of them. Additionally, in the embodiment with binocular cameras 26a and 26b and binocular viewing screens 24a and 24b the perception of depth of filed is produced.

In any case, the image may be an overlay of text or graphics or video feedback. Additionally, it is contemplated that in at least one embodiment the system described above may be used in a remote welding situation, including but not limited to robotic welding or underwater welding.

While principles and modes of operation have been explained and illustrated with regard to particular embodiments, it must be understood, however, that this may be practiced otherwise than as specifically explained and illustrated without departing from its spirit or scope.

What is claimed is:

1. A welding system comprising:
welding equipment for generating a welding current and voltage
a welding control system for controlling the welding current and voltage
a monitoring system for monitoring a welding parameter, and
a welding helmet including:
a main body
a visual display connected to the main body, and
an information generating mechanism in communication with the monitoring system generating an image representative of information from the monitoring system based upon the monitored welding parameter upon the visual display where the focus of the image is at an associated welding work area; whereby a welder may view an image representative of information about a welding operation without removing focus from the work area.

2. The welding system of claim 1 where the information generating mechanism includes an LCD display.

3. The welding system of claim 1 where the information generating mechanism includes an LED array.

4. The welding system of claim 1 where the visual display is a window including a welding lens.

5. The welding system of claim 4 where the information generating mechanism is capable of projecting a stereogram on the welding lens.

6. The welding system of claim 4 where the information generating mechanism includes a series of mirrors for reflecting the image toward the welding lens.

7. The welding system of claim 4 where the welding helmet includes a reflective surface proximate the welding lens for reflecting the image toward an interior of the welding helmet.

8. A welding system comprising:
welding equipment for generating a welding current and voltage
a welding control system for controlling the welding current and voltage
a monitoring system for monitoring a welding parameter, and
a welding helmet including:
a main body
a visual display connected to the main body, and
an information generating mechanism in communication with the monitoring system generating an image representative of information from the monitoring system based upon the monitored welding parameter upon the visual display where the focus of the image is in a focus range with an associated welding work area.

9. The welding system of claim 8 where the image includes alpha-numeric characters.

10. The welding system of claim 8 where the focus of the image is at the same focal distance as the associated welding work area.

11. The welding system of claim 8 where the visual display includes at least one video monitor for displaying a picture of the associated welding work area.

12. The welding system of claim 11 where the welding helmet further includes at least one camera connected to the main body for providing the picture.

13. The welding system of claim 11 where the information generating mechanism is capable of including the image in the picture.

14. The welding system of claim 11 where the video monitor includes an LCD display.

15. A welding assembly comprising:
   welding equipment for generating a weld, and
   a welding helmet including:
      a main body
      a visual display connected to the main body for displaying welding, and
      an information generating mechanism in communication with the welding equipment generating an image representative of information from the welding equipment based upon the welding upon the visual display where the focus of the image is in a focus range with an associated welding work area.

16. The welding system of claim 15 where the visual display includes at least one video monitor for displaying a picture of the associated welding work area.

17. The welding system of claim 16 where the information generating mechanism is capable of including the image in the picture.

18. The welding system of claim 16 where the video monitor includes an LCD display.

19. The welding system of claim 15 where the image includes alpha-numeric characters.

20. The welding system of claim 15 where the focus of the image is at the same focal distance as the associated welding work area.

\* \* \* \* \*